United States Patent [19]
Sekiya et al.

[11] 4,197,410
[45] Apr. 8, 1980

[54] N-[(N-NITROSOALKYLAMINO)METHYL]-CARBAMIC ACID ESTERS FOR GENERATING DIAZOALKANES

[75] Inventors: Minoru Sekiya; Keiichi Ito, both of Shizuoka, Japan; Yoshiyasu Terao, Hoboken, N.J.

[73] Assignee: Wako Pure Chemical Industries, Ltd., Osaka, Japan

[21] Appl. No.: 8,160

[22] Filed: Jan. 31, 1979

[30] Foreign Application Priority Data

Feb. 2, 1978 [JP] Japan ................................. 53-10767

[51] Int. Cl.$^2$ ............................................. C07C 125/06
[52] U.S. Cl. .................................... 560/159; 560/103; 260/239 AA
[58] Field of Search ................................. 560/24, 159

[56] References Cited

U.S. PATENT DOCUMENTS

| 2,683,696 | 7/1954 | Muller | 560/24 |
| 2,978,485 | 4/1961 | Frankel | 560/159 |
| 3,109,020 | 10/1963 | Frankel | 560/159 |
| 3,661,966 | 5/1972 | Bartmann | 560/159 |

FOREIGN PATENT DOCUMENTS

| 1165494 | 10/1958 | France | 560/159 |
| Ad.73625 | 9/1960 | France | 424/300 |

*Primary Examiner*—Bernard Helfin
*Assistant Examiner*—Michael Shippen
*Attorney, Agent, or Firm*—Armstrong, Nikaido, Marmelstein & Kubovcik

[57] ABSTRACT

An N-[(N-nitrosoalkylamino)methyl]carbamic acid ester of the formula:

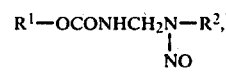

wherein $R^1$ is lower alkyl or aryl-substituted lower alkyl; and $R^2$ is lower alkyl, which is an excellent diazoalkane generating agent, can be produced by reacting a carbamic acid ester with formaldehyde and a hydrohalide of alkylamine followed by the reaction with nitrous acid, an alkali nitrite or an alkyl nitrite.

6 Claims, No Drawings

N-[(N-NITROSOALKYLAMINO)METHYL]CARBAMIC ACID ESTERS FOR GENERATING DIAZOALKANES

BACKGROUND OF THE INVENTION

This invention relates to N-[(N-nitrosoalkylamino)methyl]carbamic acid esters, a process for producing the same and a method for generating a diazoalkane by using the same.

Diazoalkanes, particularly diazomethane, are widely used as a general alkalating agent in organic syntheses.

As a diazomethane generating agent, there have been used N-nitroso compounds such as N-methyl-N-nitroso-p-toluenesulfonamide, N,N'-dimethyl-N,N'-dinitrosoterephthalamide, N-methyl-N'-nitro-N-nitrosoguanidine, N-methyl-N-nitrosourethane, and the like. But these N-nitroso compounds are unstable and easily denatured. Further, those commercially available are not pure and give out an offensive smell and are not satisfactory in generating rate of diazomethane. Recently, N-[(N-nitrosomethylamino)methyl]benzamide has been proposed as a stable diazomethane generating agent in place of these N-nitroso compounds but it is still insufficient in its generation method and the yield.

SUMMARY OF THE INVENTION

It is an object of this invention to provide N-[(N-nitrosoalkylamino)methyl]carbamic acid esters excellent as a diazoalkane generating agent. It is another object of this invention to provide a process for producing such N-[(N-nitrosoalkylamino)methyl]carbamic acid esters. It is a further object of this invention to provide a method for generating a diazoalkane by using such N-[(N-nitrosoalkylamino)methyl]carbamic acid esters.

This invention provides an N-[(N-nitrosoalkylamino)methyl]carbamic acid ester of the formula:

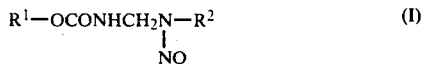

$$R^1-OCONHCH_2N-R^2 \quad (I)$$
$$\phantom{R^1-OCONHCH_2N-}|$$
$$\phantom{R^1-OCONHCH_2N-}NO$$

wherein $R^1$ is lower alkyl or aryl-substituted lower alkyl; and $R^2$ is lower alkyl, a process for producing the ester of the formula (I) and a method for generating a diazoalkane by using the ester of the formula (I).

DETAILED DESCRIPTION OF THE INVENTION

In the above-mentioned formula (I), the term "lower alkyl" means an alkyl group having 1 to 5 carbon atoms such as methyl, ethyl, n-propyl, isopropyl, n-butyl, isobutyl, pentyl, etc., and the term "aryl" means phenyl, tolyl, and the like and the term "aryl-substituted lower alkyl" means benzyl, p-methylbenzyl, and the like.

Examples of N-[(N-nitrosoalkylamino)methyl]carbamic acid esters of the formula (I) are as follows:

Methyl N-[(N-nitrosomethylamino)methyl]carbamate
Benzyl N-[(N-nitrosomethylamino)methyl]carbamate
Ethyl N-[(N-nitrosomethylamino)methyl]carbamate
Isopropyl N-[(N-nitrosomethylamino)methyl]carbamate
Butyl N-[(N-nitrosomethylamino)methyl]carbamate
Isopropyl N-[(N-nitrosoethylamino)methyl]carbamate
Isopropyl N-[(N-nitrosoisopropylamino)methyl]carbamate
Isopropyl N-[(N-nitrosobutylamino)methyl]carbamate
Isopropyl N-[(N-nitrosoisobutylamino)methyl]carbamate The compound of the formula (I) can be produced by reacting a carbamic acid ester of the formula:

$$R^1-OCONH_2 \quad (II)$$

wherein $R^1$ is as defined above, with formaldehyde and a hydrohalide of alkylamine of the formula:

$$R^2-N^+H_3X^- \quad (III)$$

wherein $R^2$ is as defined above; and X is halogen, to yield a hydrohalide of N-(alkylaminomethyl)carbamic acid ester of the formula:

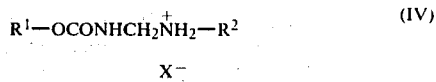

$$R^1-OCONHCH_2\overset{+}{N}H_2-R^2 \quad (IV)$$
$$X^-$$

wherein $R^1$, $R^2$ and X are as defined above, and reacting the said compound of the formula (IV) with a nitrosating agent such as nitrous acid, an alkali nitrite or an alkyl nitrite.

Examples of the carbamic acid esters of the formula (II) are isopropyl carbamate, methyl carbamate, ethyl carbamate, butyl carbamate, benzyl carbamate, etc.

Examples of the hydrohalides of alkylamine of the formula (III) are hydrochlorides of methylamine, ethylamine, isopropylamine, n-butylamine, and isobutylamine.

The first step reaction of the carbamic acid ester of the formula (II) with formaldehyde and the compound of the formula (III) can preferably be carried out in an alcohol such as methanol, ethanol, etc., at a temperature of 20° to 50° C.

In the second step of the reaction, the compound of the formula (IV) can be reacted with sodium nitrite in water, or with amyl nitrite in the presence of a base in an alcohol at a temperature of 10° to 60° C.

The compound of the formula (I) is stable and of excellent storage life without being denatured.

But the compound of the formula (I) can easily be decomposed by an alkali to yield a diazoalkane in high yield. As the alkali, there can preferably be used sodium hydroxide, potassium hydroxide, sodium alkoxides, potassium alkoxides, etc. As the solvent, there can be used water, methanol, ethanol, propanol, butanol, diethylene glycol and mixtures of those with water. Comparing with an N-[(N-nitrosoalkylamino)methyl]benzamide previously reported (i.e. the compound having $C_6H_5$ as $R^1-O-$ in the formula (I)), the compound of the formula (I) has much higher solubility in organic solvents such as alcohols, ether, benzene, etc. Owing to this higher solubility the diazoalkane generating method with the compound of the formula (I) is much more advantageous in that diazoalkane can be much more rapidly generated under milder conditions and produced in higher yield. Particularly, diazomethane can be generated in yield of as high as 80% or more, such a high yield being hardly obtained from the known compounds. From these features, the compound of the formula (I) can advantageously be applied for generating diazoalkanes in various objects under varied conditions.

This invention is illustrated in more detail by way of the following Examples.

EXAMPLES 1-9

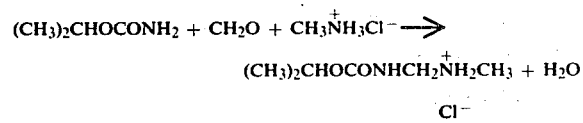

To 50 ml of ethanol, 20.3 g (0.3 mole) of methylamine hydrochloride and 30.9 g (0.36 mole) of 37% formaldehyde aqueous solution were added and the mixture was warmed to 35°–40° C. Then, a solution prepared by dissolving 30.9 g (0.3 mole) of isopropyl carbamate in 150 ml of ethanol was added dropwise to the mixture with stirring maintaining the said temperature. After the dropwise addition of the solution, stirring was continued for 1 hour with heating and then the solvent was removed by distillation under reduced pressure. The residue was recrystallized from ethanol to give 42.7 g of isopropyl N-(methylaminomethyl)carbamate hydrochloride having a melting point of 163°–164° C. in yield of 77.8%.

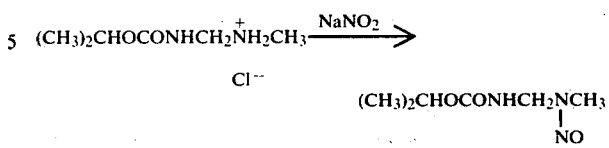

42 Grams (0.23 mole) of isopropyl N-(methylaminomethyl)carbamate hydrochloride was dissolved in 200 ml of water and 4.8 g of 35% hydrochloric acid was added thereto. To the resulting solution, 100 ml of aqueous solution containing 19 g (0.276 mole) of sodium nitrite was added dropwise with stirring at room temperature. After the dropwise addition of the sodium nitrite solution, stirring was continued for 30 minutes and deposited crystals were filtered and dried to give 24 g of isopropyl N-[(N-nitrosomethylamino)methyl]carbamate having a melting point of 66°–67° C. in yield of 60.7%.

Using the same procedures as mentioned above (Example 1), various N-[(N-nitrosoalkylamino)methyl]carbamic acid esters as listed in Table 1 were obtained by using carbamic acid esters of the formula (II) as listed in Table 1.

Table 1

| Example No. | Carbamic acid ester of the formula (II) | N-[(N-Nitrosoalkylamino)methyl]carbamic acid ester of the formula (I) Formula (Melting point) | Elementary analysis Calculated Found C (%) | H (%) | N (%) |
|---|---|---|---|---|---|
| 1 | $(CH_3)_2CHOCONH_2$ | $(CH_3)_2CHOCONHCH_2\underset{NO}{NCH_3}$ (66°–67° C.) | 41.14<br>41.21 | 7.48<br>7.46 | 23.99<br>23.80 |
| 2 | $CH_3OCONH_2$ | $CH_3OCONHCH_2\underset{NO}{NCH_3}$ (48°–49° C.) | 32.65<br>32.68 | 6.17<br>6.09 | 28.65<br>28.56 |
| 3 | $C_2H_5OCONH_2$ | $C_2H_5OCONHCH_2\underset{NO}{NCH_3}$ (38°–40° C.) | 37.26<br>37.04 | 6.88<br>6.84 | 26.07<br>25.87 |
| 4 | $n\text{-}C_4H_9OCONH_2$ | $n\text{-}C_4H_9OCONHCH_2\underset{NO}{NCH_3}$ (32°–34° C.) | 44.43<br>44.63 | 7.99<br>7.97 | 22.21<br>21.82 |
| 5 | $C_6H_5CH_2OCONH_2$ | $C_6H_5CH_2OCONHCH_2\underset{NO}{NCH_3}$ (57°–58° C.) | 53.80<br>53.73 | 5.87<br>5.85 | 18.83<br>18.81 |
| 6 | $(CH_3)_2CHOCONH_2$ | $(CH_3)_2CHOCONHCH_2\underset{NO}{NC_2H_5}$ (41°–42° C.) | 44.43<br>44.53 | 7.99<br>7.92 | 22.21<br>22.31 |
| 7 | $(CH_3)_2CHOCONH_2$ | $(CH_3)_2CHOCONHCH_2\underset{NO}{NC_3H_7}$ (30°–32° C.) | 47.28<br>47.50 | 8.43<br>8.45 | 20.68<br>20.77 |
| 8 | $(CH_3)_2CHOCONH_2$ | $(CH_3)_2CHOCONHCH_2\underset{NO}{NC_4H_9\text{-}n}$ (53°–55° C.) | 49.75<br>49.82 | 8.81<br>8.81 | 19.34<br>19.25 |
| 9 | $(CH_3)_2CHOCONH_2$ | $(CH_3)_2CHOCONHCH_2\underset{NO}{NC_4H_9\text{-}i}$ | 49.75<br>49.62 | 8.81<br>8.90 | 19.34<br>19.32 |

Table 1-continued

| | | N-[(N-Nitrosoalkylamino)methyl]carbamic acid ester of the formula (I) | | | |
|---|---|---|---|---|---|
| Example No. | Carbamic acid ester of the formula (II) | Formula (Melting point) | Elementary analysis Calculated Found | | |
| | | | C (%) | H (%) | N (%) |
| | | (55°–56° C.) | | | |

EXAMPLES 10–17

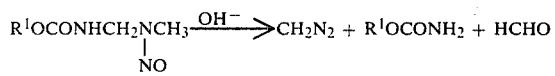

(Formaldehyde vanishes by further conversion in a strong alkaline medium).

Apparatus

A round bottom flask having a volume of 250 ml equipped with a dropping funnel and a distillation device, an end of a condenser of which was connected to a 500 ml receiver, which was connected to a 50 ml of a receiver through a gas introducing pipe which was inserted into the bottom of the 50 ml receiver.

The two receivers contained 10 ml and 20 ml of ether, respectively, and were cooled with ice-salt prior to the operation.

Procedure

To a solution obtained by dissolving 4.2 g of potassium hydroxide in a mixed solvent of 15 ml of diethylene glycol (DEG) and 3 ml of water, 50 ml of ether was added. The temperature of a water bath was maintained at 45°–50° C. and when the ether began to be distilled out, a solution prepared by dissolving 8.8 g of isopropyl N-[(N-nitrosomethylamino)methyl]carbamate in 70 ml of ether was added dropwise thereto. The ether fraction rapidly changed to yellow. After adding dropwise for 15–20 minutes, ether was added dropwise in order to make the amount of ether in the flask constant. When about 70 ml of ether was added dropwise for 20 minutes, the distillate became colorless and the reaction was completed. To the distilled ether solution containing diazomethane, benzoic acid was added to produce methyl benzoate, and an excess of benzoic acid was back-titrated with 0.2 N NaOH. The amount of the diazomethane was 1.7 g (81% yield).

By using a solvent, an alkali, and an N-[(N-nitrosoalkylamino)methyl]carbamic acid ester as listed in Table 2, diazomethane was generated according to a similar manner to that described above (Example 10). Yield of diazomethane generated is as listed in Table 2 in each case.

Table 2

| Example No. | N-[(Nitrosoalkylamino)-methyl]carbamic acid ester | Alkali | Solvent | | Yield of diazomethane |
|---|---|---|---|---|---|
| 10 | $(CH_3)_2CHOCONHCH_2NCH_3$ <br> \| <br> NO <br> (8.8 g) | KOH (4.2 g) | DEG $H_2O$ | 15 ml 3 ml | 81% |
| 11 | $CH_3OCONHCH_2NCH_3$ <br> \| <br> NO <br> (7.4 g) | KOH (4.2 g) | DEG $H_2O$ | 15 ml 3 ml | 72% |
| 12 | $C_2H_5OCONHCH_2NCH_3$ <br> \| <br> NO <br> (8.1 g) | KOH (4.2 g) | DEG $H_2O$ | 15 ml 3 ml | 70% |
| 13 | $n\text{-}C_4H_9OCONHCH_2NCH_3$ <br> \| <br> NO <br> (9.5 g) | KOH (4.2 g) | DEG $H_2O$ | 15 ml 3 ml | 61% |
| 14 | $C_6H_5CH_2OCONHCH_2NCH_3$ <br> \| <br> NO <br> (11.2 g) | KOH (4.2 g) | DEG $H_2O$ | 15 ml 3 ml | 64% |
| 15 | $(CH_3)_2CHOCONHCH_2NCH_3$ <br> \| <br> NO <br> (8.8 g) | KOH (4.2 g) | $C_4H_9OH$ | 30 ml | 77% |
| 16 | $(CH_3)_2CHOCONHCH_2NCH_3$ <br> \| <br> NO <br> (8.8 g) | NaOH (1.4 g) | $C_4H_9OH$ | 30 ml | 81% |
| 17 | $(CH_3)_2CHOCONHCH_2NCH_3$ <br> \| <br> NO | $CH_3ONa$ (3.2 g) | $CH_3OH$ | 15 ml | 82% |

Table 2-continued

| Example No. | N-[(Nitrosoalkylamino)-methyl]carbamic acid ester | Alkali | Solvent | Yield of diazomethane |
|---|---|---|---|---|
| | (8.8 g) | | | |

Note DEG = Diethylene glycol

EXAMPLES 18–21

By using an N-[(N-nitroalkylamino)methyl]carbamic acid ester, a solvent and an alkali as listed in Table 3 in place of those of Example 10, procedures similar to that of Example 10 gave diazoalkanes in yields listed in Table 3.

Table 3

| Example No. | N-[(N-Nitrosoalkylamino)-methyl]carbamic acid ester | Alkali | Solvent | Diazoalkane Yield (%) |
|---|---|---|---|---|
| 18 | $(CH_3)_2CHOCONHCH_2NC_2H_5$<br>\|<br>NO<br>(9.5 g) | KOH (4.2 g) | $C_4H_9OH$ (30 ml) | Diazoethane 50 |
| 19 | $(CH_3)_2CHOCONHCH_2NC_3H_7$<br>\|<br>NO<br>(10.2 g) | KOH (4.2 g) | $C_4H_9OH$ (30 ml) | Diazopropane 31 |
| 20 | $(CH_3)_2CHOCONHCH_2NC_4H_9$-n<br>\|<br>NO<br>(10.9 g) | KOH (4.2 g) | $C_4H_9OH$ (30 ml) | Diazobutane-n 26 |
| 21 | $(CH_3)_2CHOCONHCH_2NC_4H_9$-i<br>\|<br>NO<br>(10.9 g) | KOH (4.2 g) | $C_4H_9OH$ (30 ml) | Diazobutane-i 14 |

What is claimed is:

1. An N-[(N-nitrosoalkylamino)methyl]carbamic acid ester of the formula:

$$R^1\text{—OCONHCH}_2\text{N—R}^2 \qquad (I)$$
$$|$$
$$\text{NO}$$

wherein $R^1$ is lower alkyl or aryl-substituted lower alkyl; and $R^2$ is lower alkyl.

2. A compound according to claim 1, wherein $R^2$ is methyl.

3. A compound according to claim 1, wherein $R^1$ is isopropyl.

4. A compound according to claim 1, which is isopropyl N-[(N-nitrosomethylamino)methyl]carbamate.

5. A process for producing an N-[(N-nitrosoalkylamino)methyl]carbamic acid ester of the formula:

$$R^1\text{—OCONHCH}_2\text{N—R}^2 \qquad (I)$$
$$|$$
$$\text{NO}$$

wherein $R^1$ is lower alkyl or aryl-substituted lower alkyl; and $R^2$ is lower alkyl, which comprises reacting a carbamic acid ester of the formula:

$$R^1\text{—OCONH}_2 \qquad (II)$$

wherein $R^1$ is as defined above, with formaldehyde and a hydrohalide of alkylamine of the formula:

$$R^2\text{—N}^+\text{H}_3\text{X}^- \qquad (III)$$

wherein $R^2$ is as defined above; and X is halogen, to yield a hydrohalide of N-(alkylaminomethyl)carbamic acid ester of the formula:

$$R^1\text{—OCONHCH}_2\overset{+}{\text{N}}\text{H}_2\text{—R}^2 \qquad (IV)$$
$$X^-$$

wherein $R^1$, $R^2$ and X are as defined above, and reacting the said compound of the formula (IV) with nitrous acid, an alkali nitrite or an alkyl nitrite.

6. A process according to claim 5, wherein the carbamic acid ester of the formula (II) is methyl carbmate, ethyl carbamate, isopropyl carbamate, butyl carbamate or benzyl carbamate, and the compound of the formula (III) is methylamine hydrochloride.

* * * * *